(12) United States Patent
Morone et al.

(10) Patent No.: US 11,981,650 B2
(45) Date of Patent: May 14, 2024

(54) COUMARIN GLYOXYLATES FOR LED PHOTOCURING

(71) Applicant: IGM RESINS ITALIA S.R.L., Milan (IT)

(72) Inventors: Marika Morone, Lipomo (IT); Gabriele Pietro Norcini, Comabbio (IT); Stephen Postle, Bradenton, FL (US); Vincenzo Razzano, Bussero (IT)

(73) Assignee: IGM RESINS ITALIA S.R.L., Milan (IT)

( * ) Notice: Subject to any disclaimer, the term of this patent is extended or adjusted under 35 U.S.C. 154(b) by 0 days.

(21) Appl. No.: 17/766,346

(22) PCT Filed: Oct. 12, 2020

(86) PCT No.: PCT/IB2020/059547
§ 371 (c)(1),
(2) Date: Apr. 4, 2022

(87) PCT Pub. No.: WO2021/070152
PCT Pub. Date: Apr. 15, 2021

(65) Prior Publication Data
US 2024/0067620 A1      Feb. 29, 2024

(30) Foreign Application Priority Data
Oct. 11, 2019   (IT) .................. 102019000018575

(51) Int. Cl.
*C07D 311/08*    (2006.01)
*C09D 11/38*     (2014.01)

(52) U.S. Cl.
CPC ............ *C07D 311/08* (2013.01); *C09D 11/38* (2013.01)

(58) Field of Classification Search
CPC ..... C09D 11/101; C09D 11/322; C09D 11/38; C09D 11/40; C08K 5/07; C08K 5/10; C07D 311/08
See application file for complete search history.

(56) References Cited

U.S. PATENT DOCUMENTS 9,951,034 B2   4/2018  Morone et al.
2020/0347235 A1* 11/2020 Morone ............... C09D 11/101

FOREIGN PATENT DOCUMENTS

| EP | 2649981 | 10/2013 |
|---|---|---|
| EP | 3150641 | 4/2017 |
| WO | 20080040650 | 4/2008 |
| WO | 2014016567 | 1/2014 |
| WO | 2017216699 | 12/2017 |
| WO | 2018041935 | 3/2018 |

OTHER PUBLICATIONS

International Search Report and written opinion issued by the EPO dated Dec. 8, 2020 for PCT/I82020/059547.
Maiti Gourhari et al: "An efficient route to coumarin derivatives under dual catalysis, an organo- and a Lewi s acid catalyst", Tetrahedron, vol. 68, No. 42, 2012, pp. 8817-8822, XP028935727, ISSN: 0040-4020, DOI: 10.1016/J.TET.2012.07.092, tables 2, 3.
Ana G. Neo et al: "An easy synthesi s of diversely functionalized 2H-chromenes and amido amines by an enol-Ugi reaction", ARKIVOC, vol. 2017, No. 3, Sep. 5, 2016 (Sep. 5, 2016), pp. 21-31, XP055698974, DOI: 10.3998/ark.5550190.p009.775 abstract.
Joseph A. Van Gompel et al: "Photophysical Behavior of Ester-Substituted Aminocoumarins: A New Twist" J. Phys. Chem, Dec. 31, 1989 (Dec. 31, 1989), pp. 1292-1295, XP055698964, Retrieved from the Internet: URL:https://pubs.acs.org/doi/pdf/10.1021/j 100341a024 retrieved on May 27, 2020.
Viktor O Iaroshenko et al: "4-Chloro-3-(trifluoroacetyl)- and 4-chloro-3-(methoxalyl)coumarins as novel and efficient building blocks for the regioselective synthesis of 3,4-fused coumarins", Tetrahedron, Elsevier Science Publishers, Amsterdam, NL,vol. 67, No. 41,Aug. 10, 2011 (Aug. 10, 2011), pp. 7946-7955, XP028288347,ISSN: 0040-4020, DOI:10.1016/J.TET.2011.08.030 retrieved on Aug. 16, 2011.
International Preliminary report on patentability issued by the EPO dated Jan. 27, 2022 for PCT/IB2020/059547.

* cited by examiner

*Primary Examiner* — Thinh H Nguyen
(74) *Attorney, Agent, or Firm* — Silvia Salvadori

(57) ABSTRACT

The present invention relates to novel coumarin glyoxylates, a process for their preparation and their use as photoinitiators in photopolymerization compositions. The invention also concerns a process for the photopolymerization of compositions comprising said coumarin glyoxylates.

18 Claims, No Drawings

COUMARIN GLYOXYLATES FOR LED PHOTOCURING

This application is a U.S. national stage of PCT/IB2020/059547 filed on 12 Oct. 2020 which claims priority to and the benefit of Italian Application No. 102019000018575 filed on 11 Oct. 2019, the contents of which are incorporated herein by reference in their entireties.

DESCRIPTION

Summary of the Invention

The present invention relates to novel coumarin glyoxylates, a process for their preparation and their use as photoinitiators in photopolymerization compositions. The invention also concerns a process for the photopolymerization of compositions comprising said coumarin glyoxylates.

PRIOR ART

Photopolymerizable systems contain photoinitiators that possess a functional group which, by exposure to light radiation of appropriate wavelength, generate radicals or cause radicals to be generated by separate species that are able to initiate the polymerization.

Among the light radiation sources used in this field, light emitting diodes (LED) have been the subject of significant development over the past few years thanks to the advantages of low operation temperature and extremely long life in comparison with conventional medium pressure mercury arc curing lamps. So, LED lamps are advantageous because of the inherently small size of LED units, their longer lifetime, their robustness and their ability to be easily engineered, for example into commercial printing systems.

When using LED lamps to photocure inks and coatings, it is necessary to use specific photoinitiator systems that are tuned to the wavelength of this light source. While Mercury arc lamps have a polychromatic emission spectrum, LED lamps have only a single emission band in the range of 350-420 nm.

Photoinitiators, absorbing in the region from 350 nm to 420 nm, are thus required to use LED lamps. Moreover, since high concentration of photoactive substance are usually required for LED applications, the photoinitiators should have a high compatibility with the photopolymerizable system. Thioxanthones, such as isopropyl thioxanthone (ITX) and its derivatives, and acyl phosphine oxides are examples of photoinitiators commonly used in this field.

Unfortunately, thioxanthone derivatives are prone to yellowing upon exposure, while acyl phosphine oxide photoinitiators are oxygen sensible, and these drawbacks limit their use in most LED applications.

In the last years, various attempts were made to develop new photoinitiators able to overcome these problems, some examples of which are 3-ketocoumarins (U.S. Pat. No. 9,951,034, WO/2017/216699), acylgermanium photoinitiators (EP3150641, EP2649981), benzoyl phenyltelluride photoinitiators (Macromolecules, 2014, 47(16), 5526-5531), acylphosphine oxides (EP2877500), polycyclic glyoxylates (WO2018/041935).

In particular, the class of glyoxylates has gained attention in recent years due to their easy synthesis routes and the low yellowing properties.

Unfortunately, the new glyoxylate compounds showed to be poorly reactive under LED wavelengths.

The preparation of coumarin glyoxylate derivatives was first hypothesized in 2012 (Tetrahedron 68 (2012) 8817-8822). However, this document shows that not all the desired compounds could be prepared and, also, no experimental test relating to use/activity of the compounds disclosed therein is provided.

There is a constant need for novel photoinitiators which overcome the drawbacks of the prior art, such as yellowing and oxygen sensitivity, and which show further interesting properties, such as the reactivity also to LED wavelength and the like.

DESCRIPTION OF THE INVENTION

Surprisingly, we found that certain coumarin glyoxylates well react to UVA, UVB and UVC wavelength ranges as well as, and more preferably, react to LED sources emitting in the range from 350 to 420 nm, the latter representing a technical progress compared to prior art.

Therefore, the present invention relates to specific coumarin glyoxylates useful as photoinitiators, compositions comprising said photoinitiators, a process for their preparation and a process for the photopolymerization of compositions comprising said coumarin glyoxylates.

According to one of its aspects, the present invention relates to a photocurable composition comprising:
a) from 50 to 99.9%, preferably from 70 to 98.9% by weight, based on the total content of the composition, excluding possible water and solvents, of at least one ethylenically unsaturated compound; and
b) from 0.1 to 35%, preferably from 0.1 to 20%, and more preferably from 0.2 to 15% by weight, based on the total content of the composition, excluding possible water and solvents, of at least one compound of formula (I)

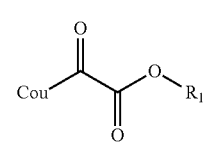

wherein:
$R_1$ is a substituted or unsubstituted C1-C20 alkyl group or a substituted or unsubstituted C1-C50 alkyl group which is interrupted by one or more oxygens and which may terminate with a hydroxy group; Cou is a coumarin group of formula:

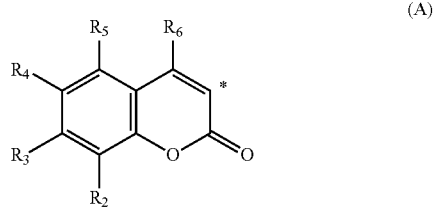

wherein:
$R_2$, $R_3$, $R_4$ and $R_5$ are, independently of one another, hydrogen, substituted or unsubstituted C1-C20 alkyl, -N(C1-C6 alkyl)$_2$, piperidino, morpholino, piperazino, —O—$R_7$ or —S—$R_7$, where $R_7$ is hydrogen, substituted or unsubstituted C1-C20 alkyl, C2-C12 alkenyl, substituted or unsubstituted aryl, heteroaryl or C5-C6 cycloalkyl;

$R_6$ is hydrogen, a hydroxy group or a C1-C4 alkyl group; or Cou is a substituted or unsubstituted naphtho-coumarin group of formula:

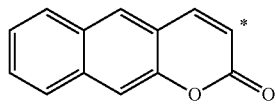

(B)

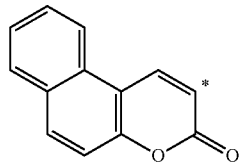

(C)

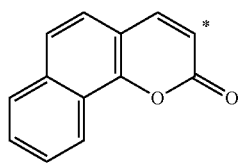

(D)

wherein the star indicates the carbon atom which is bound to the keto group of formula (I).

The expression "excluding possible water and solvents" means that the % weight amounts of the compounds and of the additional components of the composition is based on the total weight of said compounds and said additional components, irrespective of the fact that water and/or solvents can be present in the composition.

According to another of its aspects, the present invention relates to a compound of formula Ia:

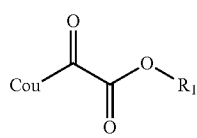

Ia wherein:

$R_1$ is a substituted or unsubstituted C1-C20 alkyl group or a substituted or unsubstituted C1-C50 alkyl group which is interrupted by one or more oxygens and which may terminate with a hydroxy group; Cou is a coumarin group of formula:

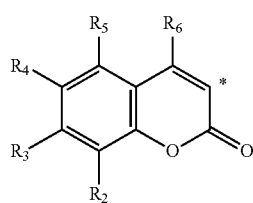

(A)

wherein:

$R_2$, $R_3$, $R_4$ and $R_5$ are, independently of one another, hydrogen, substituted or unsubstituted C1-C20 alkyl, -N(C1-C6 alkyl)$_2$, piperidino, morpholino, piperazino, —O—$R_7$ or —S—$R_7$, where $R_7$ is hydrogen, substituted or unsubstituted C1-C20 alkyl, C2-C12 alkenyl, substituted or unsubstituted aryl, heteroaryl or C5-C6 cycloalkyl;

$R_6$ is hydrogen, a hydroxy group or a C1-C4 alkyl; provided that all the following conditions (i) to (v) are met:

i. when $R_1$ is methyl, than at least one of $R_2$, $R_3$, $R_4$, $R_5$ and $R_6$ is different from hydrogen;

ii. when $R_1$ is methyl or ethyl, than $R_4$ is different from methyl;

iii. when $R_1$ is methyl, than $R_6$ is not hydroxy;

iv. when $R_1$ is methyl or ethyl, than $R_2$ is not methoxy; and v. when $R_1$ is methyl or ethyl, than $R_2$ and $R_4$ are not both tert-butyl; or Cou is a substituted or unsubstituted naphtho-coumarin group of formula:

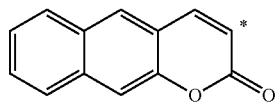

(B)

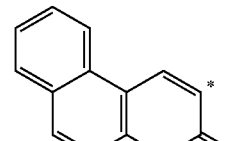

(C)

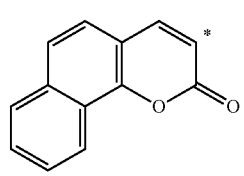

(D)

wherein the star indicates the carbon atom which is bound to the keto group of formula (Ia). According to an embodiment, in formula (Ia), when R1 is methyl, then $R_3$ is not methoxy.

According to an embodiment, C2-C12 alkenyl is C3-C12 alkenyl.

According to another of its aspects, the present invention relates to a process for the preparation of compounds of formulas (I) or (Ia) as above defined, according to the following scheme:

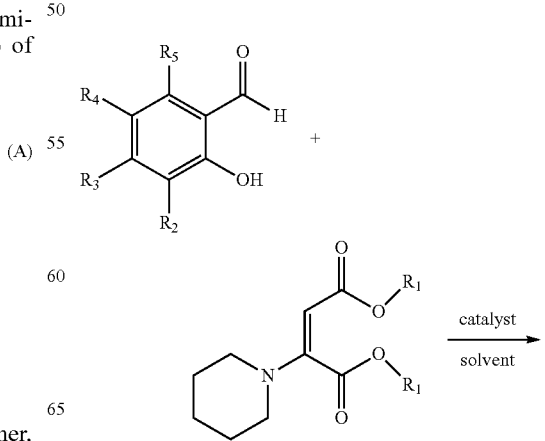

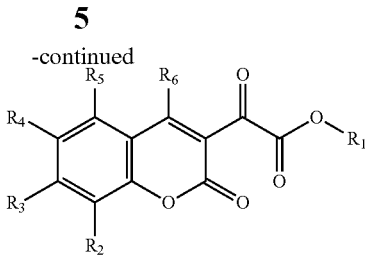

wherein:
$R_1$, $R_2$, $R_3$, $R_4$, $R_5$ and $R_6$ are as above described;
the catalyst is an acid, preferably chosen from acetic acid, formic acid, polyphosphoric acid, paratoluensulfonic acid, methanesulfonic acid, trifluoromethanesulfonic acid, trifluoroacetic acid, sulfuric acid, hydrochloric acid, phosphoric acid, hydrobromic acid, nitric acid, perchloric acid, hydrofluoric acid, nitrous acid and mixture thereof; as an alternative, the catalyst is selected from trifluoromethanesulfonic anhydride, trifluoroacetic anhydride and phosphorus pentoxide;
the solvent is and organic solvent, preferably an aromatic solvent, more preferably selected from benzene, toluene, o-xylene, m-xylene, p-xylene, xylene mixtures, chlorobenzene, 1,2-dichlorobenzene, 1,3-dichlorobenzene, 1,4-dichlorbenzene and mixtures thereof. As an alternative, the reaction may be performed without any solvent.

According to an embodiment, in the above process, the catalyst is not $FeCl_3$.

According to the present invention, the terms "photocuring" and "photopolymerizing" and related terms, are synonyms.

According to another of its aspects, the present invention relates to a process for photopolymerizing which comprises:
(i) providing a photopolymerizable composition comprising compounds (a) and (b), as above defined; and
(ii) photopolymerizing the composition of step (i) with a light source.

DETAILED DESCRIPTION OF THE INVENTION

In the present description the expressions "alkyl" or "alkyl group" mean, where not differently indicated, a linear or branched, saturated alkyl chain containing the given number of carbon atoms and includes all possibilities for each number of carbon atoms in the alkyl group, i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl, and the like.

"Alkenyl" or "alkenyl group" mean an unsaturated group containing from 3 to 12 carbon atoms, which can be, for example, allyl, methallyl or undecenyl.

The expressions "cycloalkyl" or "cycloalkyl group" mean, where not differently indicated, an aliphatic ring containing 5 or 6 carbon atoms which can be cyclopentyl or cyclohexyl.

The expressions "aryl" or "aryl group" include, but it is not limited to, for example a substituted or unsubstituted phenyl group, a substituted or unsubstituted naphthyl group, an anthracenyl group, an indenyl group, a fluorenyl group.

The expressions "heteroaryl" or "heteroaryl group" include, but it is not limited to, for example a furan, a thiophene, a pyrrole, a oxazole, an isooxazole, a thiazole, an isothiazole, an imidazole, a pyrazole, a pyrane, a pyridine, a pyrrolidine, a piperidine, an indole, a quinoline, an isoquinoline, a xanthene, a carbazole, an acridine, an indeline, an julolidine and others.

The expression "C1-C50 alkyl which is interrupted by one or more oxygens" means that, in case more than one oxygen atom is present, said oxygen atoms are separated from one another by at least one methylene group, i.e. the oxygen atoms are non-consecutive. Examples include the following:
—O—$CH_2$—$OCH_3$, —O—$CH_2CH_2$—$OCH_2CH_3$, —O—[$CH_2CH_2O$]$_v$$CH_3$, —O—[$CH_2CH_2O$]$_v$OH, —O—[$CH_2CH_2O$]$_v$$CH_2CH_3$, $CH_2$—O—[$CH_2CH_2O$]$_v$$CH_3$ with v=1-24, —O—[$CH_2CH_2CH_2O$]$_p$OH, —O—[$CH_2CH_2CH_2O$]$_p$$CH_3$, —O—[$CH_2CH_2CH_2O$]$_p$$CH_2CH_3$, —$CH_2$—O—[$CH_2CH_2CH_2O$]$_p$$CH_3$ with p=1-16.

The term "substituted" group means that said group bears one or more substituents, said substituents being preferably selected from halogen atom, alkyl, cycloalkyl, alkoxy, alkylamino, dialkylamino, alkylthio or arylthio group, heterocyclic groups, preferably selected from methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, methoxy, ethoxy, propoxy, isopropoxy, butoxy, pentyloxy, phenoxy, hydroxyl, acetoxy, —$PO_3H$, methylthio, ethylthio, i-propylthio, n-propylthio, phenyltio, mercapto, acetylthio, thiocyano, methylsulfinyl, methylsulfonyl, dimethylsulfonyl, sulfonate groups, fluorine atom, chlorine atom, bromine atom, iodine atom, trimethylsilyl, triethylsilyl, trimethylstannyl, furyl, thienyl, pyridyl, and morpholino.

Among said substituents, electron donating groups such as alkoxy groups, for example methoxy, ethoxy, isopropoxy, tert-butoxy or phenoxy groups, methyl, ethyl, isopropyl, hydroxyl, acetoxy, benzoyloxy groups, etc. or a thioalkyl group, such as methylthio, ethylthio, n-propylthio, i-propylthio, butylthio, pentylthio, or a arylthio group, such as phenylthio, are preferred.

According to preferred embodiments, in formulas (I) or (Ia) as above defined, at least one of the following condition is preferred:
$R_1$ is a substituted or unsubstituted C1-C20 alkyl group, more preferably a C1-C12 alkyl group;
Cou is a coumarin group of formula (A) in which at least one of $R_2$, $R_3$, $R_4$ and $R_5$ is different from hydrogen, more preferably a coumarin group of formula (A) in which at least one of $R_2$, $R_3$, $R_4$ and $R_5$ is —O—$R_7$ or —S—$R_7$ and $R_7$ is a C1-C20 alkyl; most preferably a coumarin group of formula (A) in which $R_3$ is —O—$R_7$ or —S—$R_7$ and $R_7$ is a C1-C20 alkyl;
$R_6$ is preferably hydrogen.
According to a preferred embodiment, two, three or all the above conditions are simultaneously met.
According to a preferred embodiment, Cou is (C).
In another preferred embodiment, in the compounds of formulas (I) or (Ia), Cou is a coumarin group of formula (A), in which $R_6$ is hydrogen, at least two of $R_2$, $R_3$, $R_4$ and $R_5$ are —O—$R_7$ group and $R_7$ and $R_1$ are a C1-C20 alkyl group.
According to a preferred embodiment, in compounds of formula (I) or (Ia), when $R_3$ is a methoxy group and $R_1$ is a methyl group, then at least one of $R_2$, $R_4$, $R_5$ and $R_6$ is not hydrogen.
In all the preferred embodiments concerning compounds of formula (Ia), the above disclosed conditions (i) to (v) must be met.

The compounds represented by formulas (I) or (Ia) can be prepared according conventional methods known to the skilled in the art as reported, for example, in Tetrahedron 68 (2012) 8817-8822.

Alternatively, the compounds may be prepared according to the process herein disclosed and claimed which, surprisingly, is also able to provide compounds that cannot be prepared according to the prior art processes (see the position of the ethylhexyl substituent of the coumarin of Example 1).

According to the invention, the photoinitiators of formulas (I) or (Ia) can be used to prepare photocurable compositions comprising ethylenically unsaturated compounds (a).

Said unsaturated compounds (a) can contain one or more olefinic double bonds. They can be low-molecular weight (monomeric) or high-molecular weight (oligomeric) compounds.

Examples of suitable low molecular weight monomers having one double bond are alkyl or hydroxyalkyl acrylates or methacrylates, such as methyl, ethyl-, butyl-, 2-ethylhexyl-, 2-hydroxyethyl-, isobornyl-acrylate and methyl or ethyl methacrylate. Further examples are resins modified with silicon or fluorine, e.g. silicone acrylates. Further examples of these monomers are acrylonitrile, acrylamide, methacrylamide, N-substituted (meth)acrylamides, styrene, alkylstyrenes and halogeno styrenes, vinyl esters such as vinyl acetate, vinyl ethers such as iso-butyl vinyl ether, N-vinylpyrrolidone, vinyl chloride or vinylidene chloride.

Examples of monomers having more than one double bond are the ethylene glycol diacrylate, propylene glycol diacrylate, neopentyl glycol diacrylate, hexamethylene glycol diacrylate, bisphenol A diacrylate, 4,4'-bis-(2-acryloyloxyethoxy)-diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris-(2-acryloylethyl) isocyanurate.

Examples of high-molecular weight (oligomeric) polyunsaturated compounds are acrylated epoxy resins, acrylated or vinyl-ether- or epoxy-group-containing polyesters, acrylated polyurethanes or acrylated polyethers. Further examples of unsaturated oligomers are unsaturated polyester resins which are usually prepared from maleic acid, phthalic acid and one or more diols and which have molecular weights of from about 500 Da to 3,000 Da. Such unsaturated oligomers can also be referred to as prepolymers.

Examples of compounds (a), which are particularly suitable for the implementation of the present invention, are esters of ethylenically unsaturated carboxylic acids and polyols or polyepoxides, and polymers containing ethylenically unsaturated groups in the chain or in side groups, e.g. unsaturated polyesters, polyamides and polyurethanes and copolymers thereof, alkyl resins, polybutadiene and butadiene copolymers, polyisoprene and isoprene copolymers, polymers and copolymers having (meth)acrylic groups in side chains, as well as mixtures thereof.

Illustrative examples of unsaturated carboxylic acids or anhydrides, useful for the preparation of the above esters, are acrylic acid, methacrylic acid, maleic anhydride, crotonic acid, itaconic acid, cinnamic acid and unsaturated fatty acids such as linolenic acid and oleic acid. Acrylic and methacrylic acid are preferred.

Examples of polyols, which can be esterified, are aromatic and aliphatic and cycloaliphatic polyols, preferably aliphatic and cycloaliphatic polyols. Aromatic polyols are, for example, hydroquinone, 4,4'-dihydroxydiphenyl, 2,2-di(4-hydroxyphenyl) propane, as well as novolaks and resoles. Polyepoxides, which can be esterified, include those based on the said polyols, especially the aromatic polyols and epichlorohydrin. Also suitable as polyols are polymers and copolymers that contain hydroxyl groups in the polymer chain or in side groups, for example polyvinyl alcohol and copolymers thereof or polymethacrylic acid hydroxyalkyl esters or copolymers thereof. Further suitable polyols are oligoesters carrying hydroxyl terminal groups.

Examples of aliphatic and cycloaliphatic polyols include alkylenediols containing preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 Da to 1,500 Da, 1,3-cyclopentanediol, 1,2-, 1,3- or 1,4-cyclohexanediol, 1,4-dihydroxymethyl cyclohexane, glycerol, tris(β-hydroxy-ethyl)amine, trimethylolethane, trimethylolpropane, pentaerythritol, dipentaerythritol and sorbitol.

Further suitable ethylenically unsaturated compounds (a) are unsaturated polyamides obtained from unsaturated carboxylic acids and aromatic, aliphatic and cycloaliphatic polyamines having preferably from 2 to 6, preferably from 2 to 4, amino groups. Examples of such polyamines are: ethylenediamine, 1,2- or 1,3-propylenediamine, 1,2-, 1,3- or 1,4-butylenediamine, 1,5-pentylenediamine, 1,6-hexylenediamine, octylenediamine, dodecylene diamine, 1,4-diaminocyclohexane, isophoronediamine, phenylene diamine, bisphenylenediamine, di-(β-aminoethyl) ether, diethylene triamine, triethylenetetramine and di(β-aminoethoxy)- and di(β-aminopropoxy)ethane. Other suitable polyamines are polymers and copolymers which may contain additional amino groups in the side chain and oligoamides containing amino end groups.

Specific examples of such unsaturated polyamides are: methylenebisacrylamide, 1,6-hexamethylene bisacrylamide, diethylenetriamine trismethacrylamide, bis(methacrylamidopropoxy) ethane and N-[(β-hydroxyethoxy)ethyl]-acrylamide.

Unsaturated polyurethanes are also suitable for the implementation of the present invention, for example those derived from saturated or unsaturated diisocyanates and unsaturated or saturated diols. Polybutadiene and polyisoprene and copolymers thereof may also be used. Suitable comonomers include, for example, olefins, such as ethylene, propene, butene and hexene, (meth)acrylates, acrylonitrile, styrene and vinyl chloride.

Polymers having unsaturated (meth)acrylate groups in the side chain can be used as component (a). They may tipically be reaction products of epoxy resins based on novolak with (meth)acrylic acid; homo- or copolymers of vinyl alcohol or hydroxyalkyl derivatives thereof that have been esterified with (meth)acrylic acid; and homo- and co-polymers of (meth)acrylates that have been esterified with hydroxyalkyl (meth)acrylates.

The photocurable compositions of the present invention can also comprise one or more of the following components: (c) photosensitizers and/or (d) accelerators/coinitiators and/or further (e) photoinitiators and/or (f) additives, in addition to compounds (a) and (b) as described above.

The photocurable compositions of the present invention can also be formulated in compositions further comprising water and/or solvents, such as organic solvents.

Photosensitizers (c) can be present in an amount comprised between 0.01 and 15% by weight, of the total content, excluding possible water and solvents, preferably between 0.01 and 10% by weight.

Examples of photosensitizers are those commonly used in the art, aromatic carbonyl compounds, e.g. benzophenones, thioxanthones, anthraquinones and 3-acylcoumarin derivatives, terphenyls, styryl ketones, and 3-(aroylmethylene)-thiazolines, camphorquinones and also eosin, rhodamine and erythrosine dyes.

Examples of thioxanthones are thioxanthone, 2-isopropyl thioxanthone, 2-chloro thioxanthone, 2-dodecyl thioxanthone, 2,4-diethyl thioxanthone, 2,4-dimethyl thioxanthone, 1-methoxycarbonyl thioxanthone, 2-ethoxycarbonyl thioxanthone, 3-(2-methoxyethoxycarbonyl) thioxanthone, 4-butoxycarbonyl thioxanthone, 3-butoxycarbonyl-7-methyl thioxanthone, 1-cyano-3-chloro thioxanthone, 1-ethoxycarbonyl-3-chloro thioxanthone, 1-ethoxycarbonyl-3-ethoxy thioxanthone, 1-ethoxycarbonyl-3-amino thioxanthone, 1-ethoxycarbonyl-3-phenylsulfuryl thioxanthone, 3,4-di[2-(2-methoxyethoxy)ethoxycarbonyl] thioxanthone, 1-ethoxycarbonyl-3-(1-methyl-1-morpholinoethyl) thioxanthone, 2-methyl-6-dimethoxymethyl thioxanthone, 2-methyl-6-(1,1-dimethoxybenzyl) thioxanthone, 2-morpholinomethyl thioxanthone, 2-methyl-6-morpholinomethyl thioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxy thioxanthone, 6-ethoxycarbonyl-1-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride, or those described in the patent application PCT/EP2011/069514, such as n-dodecyl-7-methyl-thioxanthone-3-carboxylate and N,N-disobutyl-7-methyl-thioxanthone-3-carbamide. Also suitable are polymeric thioxanthone derivatives (e.g. Omnipol® TX from IGM Resins B. V., Genopol® TX-1 from Rahn A. G., Speedcure® 7010 from Lambson Limited).

Examples of benzophenones are benzophenone, 4-phenyl benzophenone, 4-methoxy benzophenone, 4,4'-dimethoxybenzophenone, 4,4'-dimethyl benzophenone, 4,4'-dichloro benzophenone, 4,4'-dimethylamino benzophenone, 4,4'-diethylamino benzophenone, 4-methyl benzophenone, 2,4,6-trimethyl benzophenone, 4-(4-methylthiophenyl) benzophenone, 3,3'-dimethyl-4-methoxy benzophenone, methyl 2-benzoyl benzoate, 4-(2-hydroxyethylthio) benzophenone, 4-(4-tolylthio) benzophenone, 4-benzoyl-N,N,N-trimethylbenzene methanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl) benzophenone, 4-benzoyl-N,N-dimethyl-N-[2-(1-oxo-2-propenyl)oxyethyl-benzene methanaminium chloride. Also suitable are polymeric benzophenone derivatives (e.g. Omnipol® BP, Omnipol® 2702 and Omnipol® 682 all from IGM Resins B. V., Genopol® BP-2 from Rahn A. G. and Speedcure® 7005 from Lambson Limited).

Examples of 3-acylcoumarin derivatives are 3-benzoyl coumarin, 3-benzoyl-7-methoxy coumarin, 3-benzoyl-5,7-di(propoxy) coumarin, 3-benzoyl-6,8-dichloro coumarin, 3-benzoyl-6-chloro coumarin, 3,3'-carbonyl-bis[5,7-di(propoxy) coumarin], 3,3'-carbonyl-bis(7-methoxy coumarin), 3,3'-carbonyl-bis(7-diethylamino coumarin), 3-isobutyroyl coumarin, 3-benzoyl-5,7-dimethoxy coumarin, 3-benzoyl-5,7-diethoxy coumarin, 3-benzoyl-5,7-dibutoxy coumarin, 3-benzoyl-5,7-di(methoxyethoxy) coumarin, 3-benzoyl-5,7-di(allyloxy) coumarin, 3-benzoyl-7-dimethylamino coumarin, 3-benzoyl-7-diethylamino coumarin, 3-isobutyroyl-1,7-dimethylamino coumarin, 5,7-dimethoxy-3-(1-naphthoyl) coumarin, 5,7-dimethoxy-3(1-naphthoyl)-coumarin, 3-benzoylbenzo [f]coumarin, 7-diethylamino-3-thienoyl coumarin, 3-(4-cyanobenzoyl)-5,7-dimethoxy coumarin, or those described in EP2909243 and WO2017216699.

Examples of 3-(aroylmethylene) thiazolines are 3-methyl-1,2-benzoylmethylene-β-naphtho thiazoline, 3-methyl-2-benzoylmethylene-benzo thiazoline, 3-ethyl-2-propionylmethylene-β-naphtho thiazoline. Examples of other aromatic carbonyl compounds are acetophenone, 3-methoxyacetophenone, 4-phenylacetophenone, benzil, such as that described in WO 2013/164394, 2-acetylnaphthalene, 2-naphthaldehyde, 9,10-anthraquinone, 9-fluorenone, dibenzosuberone, xanthone, 2,5-bis(4-diethylaminobenzylidene) cyclopentanone, α-(para-dimethylamino benzylidene), ketones, such as 2-(4-dimethylamino-benzylidene)-indan-1-one or 3-(4-dimethylaminophenyl)-1-indan-5-yl-propenone, 3-phenylthiophthalimide, N-methyl-3,5-di(ethylthio)phthalimide.

Particularly preferred are thioxanthones and 3-acylcoumarins.

The above components (c) increase the activity of photoinitiators (b) without shortening the shelf life of the compositions. Moreover, said compositions have the special advantage that an appropriate choice of the photosensitizer (c) allows the spectral sensitivity of photoinitioator (b) to be shifted to any desired wavelength region. The skilled in the art is able to select the suitable photosensitizer (c) to make the photoinitiator(s) (b) work at any desired wavelength region.

The accelerators/coinitiators (d), can be present in an amount comprised between 0.2 and 15% by weight, of the total content of the composition, excluding possible water and solvents, preferably from 0.2 to 8% by weight.

Examples of suitable accelerators/coinitiators are alcohols, thiols, thioethers, amines or ethers that have an available hydrogen, bonded to a carbon adjacent to the heteroatom, disulfides and phosphines, e.g. as described in EP 438 123 and GB 2 180 358.

Suitable examples of amine accelerators/co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cyclohexyl amine, benzyldimethyl amine, di-cyclohexyl amine, N-phenyl glycine, triethyl amine, phenyl-diethanol amine, triethanolamine, piperidine, piperazine, morpholine, pyridine, quinoline, esters of dimethylamino benzoic acid, Michler's ketone (4,4'-bis-dimethyl aminobenzophenone) and derivatives thereof.

As the amine accelerators/co-initiators, an amine-modified acrylate compound can be used; examples of such amine-modified acrylate include acrylates modified by reaction with a primary or secondary amine that are described in U.S. Pat. No. 3,844,916, EP 280222, U.S. Pat. No. 5,482,649 or U.S. Pat. No. 5,734,002.

Multifunctional amine and polymeric amine derivatives are also suitable as co-initiators some examples are Omnipol® ASA from IGM Resins B. V., Genopol® AB-2 from Rahn A. G., Speedcure® 7040 from Lambson Limited or those described in US2013/0012611.

The further photoinitiators (e) can be present in an amount comprised between 0.5 and 15% by weight, of the total content of the composition, excluding possible water and solvents, preferably between 1 and 10% by weight of the composition.

Examples of other suitable photoinitiators (e) are camphorquinone, benzophenone, benzophenone derivatives, acetophenone, acetophenone derivatives, dialkoxyacetophenones, α-hydroxyketones, α-aminoketones, 4-aroyl-1,3-dioxolanes, benzoin alkyl ethers and benzil ketals, e.g. benzil dimethyl ketal, ketosulfones, e.g 1-[4-[(4-benzoyl-phenyl)-thio]-phenyl]-2-methyl-2-[(4-methyl-phenyl)-sulfonyl]-propan-1-one (Esacure® 1001, from IGM Resins B. V.), 3-ketocoumarins, for example as described in EP2909243 and WO2017216699, phenylglyoxylates and derivatives thereof, dimeric phenyl glyoxylates, peresters, e.g. benzophenonetetracarboxylic acid peresters, for example as described in EP 126 541, acylphosphine photoinitiators (which can be chosen among mono-acylphosphine oxides, bis-acylphosphine oxides, tris-acylphosphine oxides and multifunctional mono- or bisacylphosphine oxides), halomethyltriazines, hexaaryl bisimidazole/coinitiator systems, e.g. ortho-chlorohexaphenylbisimidazole in combination with 2-mercaptobenzothiazole, ferrocenium compounds or titanocenes, for example dicyclopentadienyl-bis(2,6-difluoro-3-pyrrolophenyl)titanium, O-acyloxime ester photoinitiators.

Examples of α-hydroxyketones and α-aminoketones are 1-hydroxy cyclohexylphenyl ketone, 2-hydroxy-2-methyl-1-phenyl-propane-1-one, 1-[4-(2-hydroxyethoxy)phenyl]-2-hydroxy-2-methyl-1-propane-1-one, 2-hydroxy-1-(4-[4-(2-hydroxy-2-methyl-propionyl)-benzyl]phenyl)-2-methyl-propane-1-one), 2-hydroxy-1-(4-[4-(2-hydroxy-2-methyl-propionyl)-phenoxy]-phenyl)-2-methyl-propan-1-one, 2-methyl-1-(4-methylthiophenyl)-2-morpholinopropane-1-one), 2-benzyl-2-dimethylamino-1-(4-morpholinophenyl)-butane-1-one, and (2-(dimethylamino)-2-[(4-methylphenyl) methyl]-1-[4-(4-morpholinyl) phenyl]-1-butanone).

Examples of O-acyloxime ester photoinitiators are 1,2-octanedione,1-[4-(phenylthio)phenyl]-2-(O-benzoyloxime), ethanone 1-[9-ethyl-6-(2-methylbenzoyl)-9H-carbazole-3-yl] 1-(O-acetyloxime) or those described in GB 2339571.

Examples of acylphosphine photoinitiators include, but are not limited to, bis(2,4,6-trimethylbenzoyl)phenylphosphine oxide, bis(2,6-dimethoxybenzoyl)-2,4,4-trimethylpentyl phosphine oxide, bis(2,4,6-trimethylbenzoyl)-(2,4-dipentyloxyphenyl), 2,4,6-trimethylbenzoyl-diphenyl phosphine oxide and ethyl (2,4,6-trimethylbenzoyl) phenylphosphinate, Phenyl(2,4,6-trimethylbenzoyl)phosphinic acid, glycerol ethoxylated trimester (Omnipol® TP from IGM Resins B. V.).

Examples of the halomethyltriazines based photoinitiators are 2-[2-(4-methoxy-phenyl)-vinyl]-4,6-bis-trichloromethyl [1,3,5]triazine, 2-(4-methoxy-phenyl)-4,6-bis-trichloromethyl [1,3,5]triazine, 2-(3,4-dimethoxyphenyl)-4,6-bis-trichloromethyl [1,3,5]triazine, 2-methyl-4,6-bis-trichloromethyl [1,3,5] triazine.

Cationic photoinitiators can be also used as the further photoinitiators (e), when the photocurable compositions according to the invention are used in hybrid systems (which in this connection mean mixtures of free-radically and cationically curing systems). Examples of suitable cationic photoinitiators are aromatic sulfonium, phosphonium or iodonium salts, as described e.g. in U.S. Pat. No. 4,950,581, or cyclopentadienylarene-iron(II) complex salts, e.g. ($\eta^6$-isopropylbenzene)($q^5$-cyclopentadienyl) iron(II) hexafluorophosphate or photolatent acids based on oximes, as described, for example, in GB 2 348 644, U.S. Pat. Nos. 4,450,598, 4,136,055, WO 00/10972 and WO 00/26219.

Additives (f) can be, for example, thermal initiators, binders, stabilizers, and mixture thereof.

The photocuring process according to the invention, especially in the case of pigmented compositions, may also be assisted by the addition, as additional additive (f), of a thermal initiator, a compound that forms free radicals when heated, e.g. an azo compounds, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

Binders may also be added to the photocurable composition of the invention. The addition of binders is particularly advantageous when the photocurable compounds are liquid or viscous substances. The amount of binder may be, for example, from 5 to 60% by weight, preferably from 10 to 50% by weight, based on the total weight of the composition, excluding possible water and solvents. The choice of binder is made in accordance with the field of use and the properties required therefor, such as developability in aqueous and organic solvent systems, adhesion to substrates and sensitivity to oxygen.

Suitable binders are, for example, polymers having a weight average molecular weight (Mw) of approximately from 5,000 Da to 2,000,000 Da, preferably from 10,000 Da to 1,000,000 Da. Illustrative examples are: homo- and copolymers of acrylates and methacrylates, e.g. copolymers of methyl methacrylate/ethyl acrylate/methacrylic acid, poly (methacrylic acid alkyl esters), poly(acrylic acid alkyl esters); cellulose esters and ethers, such as cellulose acetate, cellulose acetate butyrate, methylcellulose, ethylcellulose, polyvinylbutyral, polyvinylformal, cyclised rubber, polyethers such as polyethylene oxide, polypropylene oxide, polytetrahydrofuran, polystyrene, polycarbonates, polyurethanes, chlorinated polyolefins, e.g. polyvinyl chloride, co-polymers of vinyl chloride/vinylidene chloride, co-polymers of vinylidene chloride with acrylonitrile, methyl methacrylate and vinyl acetate, polyvinyl acetate, co-poly (ethylene/vinyl acetate), polymers such as polycaprolactam and poly (hexamethylene adipamide), polyesters such as poly (ethylene glycol terephthalate) and poly(hexamethylene glycol succinate).

Suitable stabilizers are, for example, thermal inhibitors, such as hydroquinone, hydroquinone derivatives, p-methoxyphenol, β-naphthol or sterically hindered phenols, e.g. 2,6-di(tert-butyl)-β-cresol, which prevent premature polymerization. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N,N-diethylhydroxylamine. For the purpose of excluding atmospheric oxygen during polymerization it is possible to add paraffin or similar wax-like substances which, being insoluble in the polymer, migrate to the surface at the beginning of the polymerization and form a transparent surface layer which prevents air from entering.

It is also possible to add a light stabilizer, such as UV absorbers, e.g. hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The photocurable compositions according to the invention may also comprise, as further additives (f), photoreducible dyes, e.g. a xanthene, benzoxanthene, benzothioxanthene, thiazine, pyronin, porphyrin or acridine dye, and/or radiation cleavable trihalomethyl compounds. These compounds are described, for example, in EP445624.

Further customary additives (f) are, depending upon the intended use, optical brighteners, fillers, pigments, both white and colored pigments, colorants, antistatics, wetting agents or flow improvers. Additives customary in the art, e.g. antistatics, flow improvers and adhesion enhancers, can also be used.

It is also possible for chain-transfer reagents customary in the art to be added to the compositions according to the invention. Examples are mercaptans, amines and benzothiazole.

The composition of the invention may also comprise colorants and/or colored pigments. Depending upon the intended use, both inorganic and organic pigments may be used. Such additives will be known to the person skilled in the art; some examples are carbon black, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments. The pigments may be used in the formulations on their own or in admixture.

Depending upon the intended use, the pigments can be added to the formulations in amounts customary in the art, for example in an amount from 0.1 to 30% by weight or from 10 to 25% by weight, based on the total weight of the composition, excluding possible water and solvents.

The composition may also comprise, for example, organic colorants of an extremely wide variety of classes. Examples are azo dyes, methine dyes, anthraquinone dyes and metal complex dyes. Usual concentrations are, for example, from 0.1 to 20% wt, especially from 1 to 5% wt, based on the total weight of the composition.

The choice of additives is governed by the field of use in question and the properties desired for that field. The additives (f) described above are known in the art and are accordingly used in the amounts customary in the art.

The photocurable compositions of the invention may comprise water.

The photocurable compositions of the invention are suitable for various purposes, for example as a printing ink, such as screen printing inks, flexographic printing inks, offset printing inks and inkjet printing inks, as clearcoats, as colored coats, for example for wood or metal, as powder coatings, as coating materials inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as photoresists, e.g. galvanoresists, as etch resists or permanent resists, both liquid and dry films, as photostructurable dielectrics, and as solder masks for electronic circuits, as resists in the production of color filters for any type of display screen or in the creation of structures during the manufacture of plasma displays and electroluminescent displays, in the production of optical switches, optical gratings (interference gratings), in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibers and/or other fibers and other adjuvants) and other methods of printing in three dimensions well-known to one skilled in the art, in the coating or sealing of electronic components or as coatings for optical fibers.

The photocurable compositions of the invention are also suitable for the production of optical lenses, e.g. contact lenses or Fresnel lenses, in the manufacture of medical apparatus, aids or implants, in dry film paints.

The photocurable compositions of the invention are also suitable for the preparation of gels having thermotropic properties. Such gels are described for example in DE 19700064 and EP 678534.

Any article comprising a compound of formulas (I) or (Ia) or a photocurable compositions of the invention represents a further subject-matter of the invention.

The compounds and compositions according to the invention may also be used as free-radical photoinitiators or photoinitiating systems for radiation-curable powder coatings.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied e.g. by imagewise exposure.

According to another of its aspects, it is a further subject-matter of the invention a process for photocuring photopolymerizable compositions and inks, which process comprises:
 (i) providing a photopolymerizable composition comprising:
  compounds (a) and (b) as described above; or
  compounds (a), (b) as described above and one or more components selected from (c), (d), (e) and (f) as described above; (ii) photopolymerizing the composition of step (i) with a light source.

According to a preferred embodiment, the photopolymerizable composition used in step (i) above comprises at least (a), (b) and (d) as above described.

The term "providing" in the first step of the above method is intended to include either preparing said composition or obtaining said composition by any other possible way, such as purchase and the like.

According to one embodiment, said light source comprises UV light in at least one of the UVA, UVB and UVC ranges.

According to a preferred embodiment, said light source is a LED source, particularly preferred are LED light source emitting at wavelengths comprised between 365 nm and 400 nm, more preferably 365 nm, 385 nm and 395 nm.

According to the invention the distance between the lamp and the substrate to be exposed may vary according to the intended use and the type and strength of the lamp, e.g. from 0.1 cm to 150 cm, preferably from 1 cm to 50 cm.

Said photopolymerizable composition may also be applied over a substrate already comprising a coated or printed layer. Said photopolymerizable composition may, after photopolymerization with said light source, be overprinted or overcoated with one or more compositions suitable for printing or coating.

The article obtained by applying said photopolymerizable composition to said substrate by said means of coating or printing, and photopolymerizing by said light source, with or without further elaboration of the article by further coating or printing, is a further subject-matter of this invention.

Surprisingly, we found that compounds of formulas (I) and (Ia) are active as photoinitiatiors and their activity is higher than that of glyoxylate compounds described in literature (WO2018/041935). Moreover, compounds of formulas (I) and (Ia) are very reactive with LED lamps both in clear and pigmented systems.

The invention is illustrated in detail below by the following examples, which are illustrative and not limiting.

In case of inconsistencies between the chemical name and the chemical structure herein indicated, the chemical structure prevails.

EXAMPLES

1H NMR spectra were recorded with a Bruker Avance 400 MHz or a Bruker DMX 500 MHz or a Bruker DMX 600 MHz.

Infrared spectra were recorded with a FT-IR 430-Jasco.

Example 1

Synthesis of methyl 2-[7-(2-ethylhexyloxy)-2-oxo-2H-chromen-3-yl]-2-oxoacetate

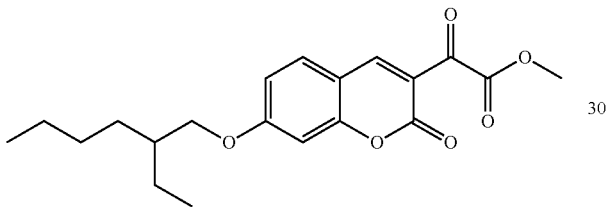

6.35 g (27.94 mmoles) of 1,4-dimethyl (2E)-2-(piperidin-1-yl)but-2-enedioate (prepared as reported in Chem Res Chin Univ 2015, 31(2), 212-217) and 7.00 g (27.96 mmoles) of 4-[(2-ethylhexyl)oxy]-2-hydroxybenzaldehyde were melted under stirring at 80° C. Then 7.0 mL of acetic acid were added to the mixture. The reaction temperature was raised up to 110° C. and the mixture stirred for 1 hour. After completion of the reaction, the mixture was cooled to 35-40° C., dissolved in 200 mL of dichloromethane and washed with 400 mL (x2) of water. The organic layer was dried over anhydrous sodium sulfate, filtered and the solvent removed by distillation under vacuum. The crude product was purified by crystallization from ethanol obtaining 5.00 g of a yellow solid (yield 50%). $^1$H-NMR (CDCl3, δ ppm): 0.90 (m, 6H), 1.25-1.50 (m, 8H), 1.75 (m, 1H), 3.93-3.96 (m, 5H), 6.85 (d, 1H), 6.92 (dd, 1H), 7.55 (d, 1H), 8.52 (s, 1H).

Example 2

Synthesis of methyl 2-[7-(2-ethylhexyl-sulfanyl)-2-oxo-2H-chromen-3-yl]-2-oxoacetate

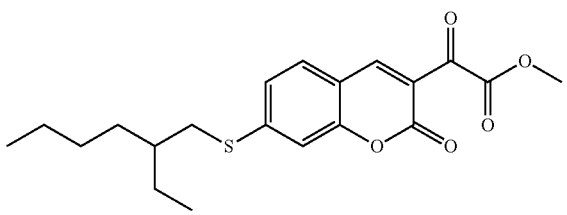 [SMILES: CCCCC(CC)COc1ccc2cc(C(=O)C(=O)OC)c(=O)oc2c1]

2.74 g (16.89 mmoles) of anhydrous iron(III) chloride were added in small portions under stirring to a warm solution of 4.50 g (16.89 mmoles) of 4-[(2-ethylhexyl)sulfanyl]-2-hydroxybenzaldehyde and 3.84 g (16.90 mmoles) of 1,4-dimethyl (2E)-2-(piperidin-1-yl)but-2-enedioate in 50 mL of toluene. The reaction mixture was refluxed for 5 hours under nitrogen atmosphere. Progress of the reaction was monitored by TLC. Then the reaction mixture was allowed to cool, quenched with 200 mL of water and extracted with 250 mL of ethyl acetate. The emulsion obtained during the work-up was filtered through a pad of celite and the phases were separated. The organic layer was dried over anhydrous sodium sulfate, filtered and the solvent removed by distillation under vacuum. The crude product was purified by flash column chromatography on silica gel (toluene/ethyl acetate 97.5:2.5) followed by crystallization from ethanol obtaining 0.55 g of a yellow solid (yield 9%).

$^1$H-NMR (CDCl3, δ ppm): 0.90 (m, 6H), 1.25-1.50 (m, 8H), 1.70 (m, 1H), 3.00 (d, 2H), 3.95 (s, 3H), 7.15 (s, 1H), 7.20 (d, 1H), 7.50 (d, 1H), 8.50 (s, 1H).

Example 3

Synthesis of 2-ethylhexyl 2-oxo-2-(2-oxo-2H-chromen-3-yl)acetate

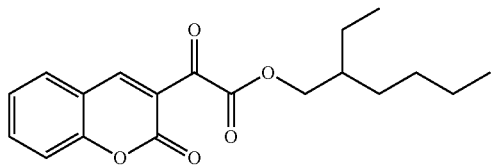 [SMILES: CCCCC(CC)COC(=O)C(=O)c1cc2ccccc2oc1=O]

0.17 g (0.35 mmoles) of zirconium(IV) acetylacetonate were added under stirring to a warm solution of 0.80 g (3.45 mmoles) of methyl 2-oxo-2-(2-oxo-2H-chromen-3-yl)acetate (prepared as reported in Tetrahedron 2012, 68, 8817-8822) and 0.90 g (6.91 mmoles) of 2-ethyl-1-hexanol in 15 mL of toluene. The reaction mixture was stirred at 105° C. for 1.5 hours eliminating methanol by distillation. Progress of the reaction was monitored by TLC. After completion of the reaction, the mixture was allowed to cool, diluted with dichloromethane and washed with water. The organic layer was dried over anhydrous sodium sulfate, filtered and the solvent removed by distillation under vacuum. The crude product was purified by flash column chromatography on silica gel (toluene/ethyl acetate 98:2) obtaining 0.73 g of a white-yellow solid (yield 64%).

$^1$H-NMR (CDCl3, δ ppm): 0.90 (m, 6H), 1.25-1.45 (m, 8H), 1.72 (m, 1H), 4.30 (m, 2H), 7.40 (m, 2H), 7.70 (m, 2H), 8.55 (s, 1H).

Example 4

Synthesis of methyl 2-[7-(diethylamino)-2-oxo-2H-chromen-3-yl]-2-oxoacetate

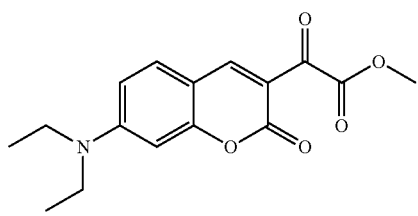 [SMILES: CCN(CC)c1ccc2cc(C(=O)C(=O)OC)c(=O)oc2c1]

7.14 g (44.02 mmoles) of anhydrous iron(III) chloride were added in small portions under stirring to a warm solution of 4.25 g (21.99 mmoles) of 4-(diethylamino) salicylaldehyde and 5.00 g (22.00 mmoles) of 1,4-dimethyl (2E)-2-(piperidin-1-yl)but-2-enedioate in 50 mL of toluene. The reaction mixture was refluxed for 3.5 hours under nitrogen atmosphere. Progress of the reaction was monitored by TLC. Then the reaction mixture was allowed to cool, quenched with 250 mL of sodium bicarbonate saturated solution and extracted with 250 mL of ethyl acetate. The emulsion obtained during the work-up was filtered through a pad of celite and the phases were separated. The organic layer was dried over anhydrous sodium sulfate, filtered and the solvent removed by distillation under vacuum. The crude product was purified by flash column chromatography on silica gel (toluene/ethyl acetate 85:15) followed by crystallization from toluene obtaining 1.10 g of a rusty solid (yield 16%).

$^1$H-NMR (CDCl3, δ ppm): 1.25 (t, 6H), 3.50 (q, 4H), 3.95 (s, 3H), 6.50 (d, 1H), 6.65 (dd, 1H), 7.42 (d, 1H), 8.42 (s, 1H).

Example 5

Synthesis of 2-ethylhexyl 2-[7-(diethylamino)-2-oxo-2H-chromen-3-yl]-2-oxoacetate

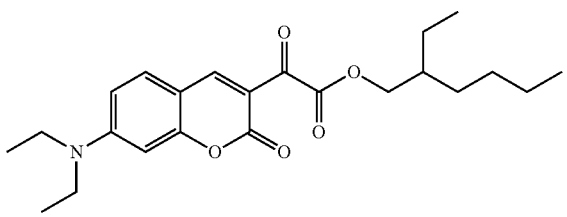 [SMILES: CCCCC(CC)COC(=O)C(=O)c1cc2ccc(N(CC)CC)cc2oc1=O]

0.22 g (0.45 mmoles) of zirconium(IV) acetylacetonate were added under stirring to a warm solution of 0.70 g (2.31 mmoles) of methyl 2-[7-(diethylamino)-2-oxo-2H-chromen-3-yl]-2-oxoacetate and 0.90 g (6.91 mmoles) of 2-ethyl-1-hexanol in 12 mL of toluene. The reaction mixture was stirred at 105° C. for 4 hours eliminating methanol by distillation.

Progress of the reaction was monitored by TLC. After completion of the reaction, the mixture was allowed to cool, diluted with dichloromethane and washed with water. The organic layer was dried over anhydrous sodium sulfate, filtered and the solvent removed by distillation under vacuum. The crude product was purified by flash column chromatography on silica gel (petroleum ether/ethyl acetate 70:30) obtaining 0.82 g of an orange-yellow solid (yield 88%).

$^1$H-NMR (CDCl3, δ ppm): 0.90 (m, 6H), 1.25 (t, 6H), 1.25-1.45 (m, 8H), 1.70 (m, 1H), 3.45 (q, 4H), 4.25 (m, 2H), 6.50 (d, 1H), 6.65 (dd, 1H), 7.42 (d, 1H), 8.40 (s, 1H).

Example 6

Synthesis of methyl 2-(5,7-dimethoxy-2-oxo-2H-chromen-3-yl)-2-oxoacetate

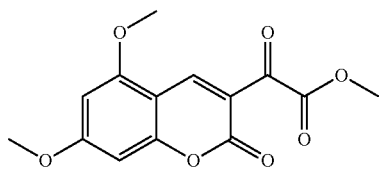

5.00 g (22.00 mmoles) of 1,4-dimethyl (2E)-2-(piperidin-1-yl)but-2-enedioate and 4.00 g (21.96 mmoles) of 2-hydroxy-4,6-dimethoxybenzaldehyde were melted under stirring at 80-100° C. Then 5.5 mL of acetic acid were added to the mixture. The reaction temperature was raised up to 110° C. and the mixture stirred for 1.5 hours. After completion of the reaction, the mixture was cooled to 35-40° C., dissolved in 200 mL of dichloromethane and washed with 400 mL (x2) of water. The organic layer was dried over anhydrous sodium sulfate, filtered and the solvent removed by distillation under vacuum. The crude product was purified by crystallization from toluene obtaining 2.60 g of a yellow solid (yield 41%).

$^1$H-NMR (CDCl3, δ ppm): 3.90 (s, 3H), 3.93 (s, 3H), 3.95 (s, 3H), 6.28 (d, 1H), 6.43 (d, 1H), 8.87 (s, 1H).

Example 7

Synthesis of 2-ethylhexyl 2-(5,7-dimethoxy-2-oxo-2H-chromen-3-yl)-2-oxoacetate

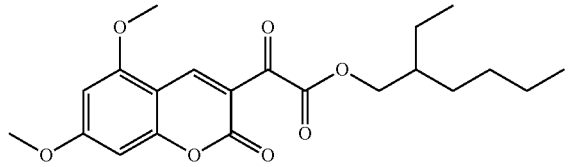 [SMILES: CCCCC(CC)COC(=O)C(=O)c1cc2c(OC)cc(OC)cc2oc1=O]

0.42 g (0.86 mmoles) of zirconium(IV) acetylacetonate were added under stirring to a warm solution of 2.50 g (8.55 mmoles) of methyl 2-(5,7-dimethoxy-2-oxo-2H-chromen-3-yl)-2-oxoacetate and 2.79 g (21.42 mmoles) of 2-ethyl-1-hexanol in 25 mL of toluene. The reaction mixture was stirred at 105° C. for 2 hours eliminating methanol by distillation.

Progress of the reaction was monitored by TLC. After completion of the reaction, the mixture was allowed to cool, diluted with dichloromethane and washed in sequence with 1M hydrochloric acid and brine. The organic layer was dried over anhydrous sodium sulfate, filtered and the solvent removed by distillation under vacuum. The crude product was purified by crystallization from ethanol obtaining 2.00 g of a yellow solid (yield 60%).

¹H-NMR (CDCl3, δ ppm): 0.86-0.92 (m, 6H), 1.26-1.46 (m, 8H), 1.70 (m, 1H), 3.90 (s, 3H), 3.93 (s, 3H), 4.24-4.31 (m, 2H), 6.28 (d, 1H), 6.44 (d, 1H), 8.88 (s, 1H).

Example 8

Synthesis of methyl 2-(7-ethoxy-2-oxo-2H-chromen-3-yl)-2-oxoacetate

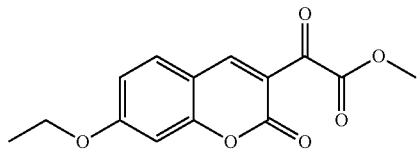 [SMILES: CCOc1ccc2cc(C(=O)C(=O)OC)c(=O)oc2c1]

6.15 g (27.06 mmoles) of 1,4-dimethyl (2E)-2-(piperidin-1-yl)but-2-enedioate and 4.50 g (27.08 mmoles) of 4-ethoxy-2-hydroxybenzaldehyde were melted under stirring at 80° C. Then 7.0 mL of acetic acid were added to the mixture. The reaction temperature was raised up to 110° C. and the mixture stirred for 1.5 hours. After completion of the reaction, the mixture was cooled to 35-40° C., dissolved in 200 mL of dichloromethane and washed with 400 mL (x2) of water. The organic layer was dried over anhydrous sodium sulfate, filtered and the solvent removed by distillation under vacuum. The crude product was purified by crystallization from toluene obtaining 3.53 g of a yellow solid (yield 47%).

¹H-NMR (CDCl3, δ ppm): 1.47 (t, 3H), 3.95 (s, 3H), 4.15 (q, 2H), 6.82 (d, 1H), 6.91 (dd, 1H), 7.56 (d, 1H), 8.50 (s, 1H).

Example 9

Synthesis of

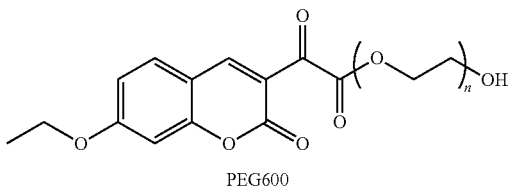

PEG600

0.62 g (1.27 mmoles) of zirconium(IV) acetylacetonate were added under stirring to a warm solution of 3.50 g (12.67 mmoles) of methyl 2-(7-ethoxy-2-oxo-2H-chromen-3-yl)-2-oxoacetate and 19.01 g (31.68 mmoles) of polyethylene glycol 600 in 35 mL of toluene. The reaction mixture was stirred at 105° C. for 1.5 hours eliminating methanol by distillation. Progress of the reaction was monitored by TLC. After completion of the reaction, the mixture was allowed to cool and the solvent removed by distillation under vacuum. The residue was dissolved in 200 mL of dichloromethane/EtOAc (2:1) and washed in sequence with 200 mL of 1M hydrochloric acid and then with 200 mL (x4) of water. The organic layer was dried over anhydrous sodium sulfate, filtered and the solvent removed by distillation under vacuum obtaining 8.62 g of a yellow oil (yield 81%).

¹H-NMR (CDCl3, δ ppm): 1.42 (t, 3H), 3.52-3.63 (m, 46H), 3.66 (t, 2H), 3.76 (t, 2H), 4.10 (q, 2H), 4.46 (t, 2H), 6.77 (d, 1H), 6.86 (dd, 1H), 7.52 (d, 1H), 8.47 (s, 1H).

Example 10

Synthesis of methyl 2-oxo-2-(3-oxo-3H-benzo[f]chromen-2-yl)acetate

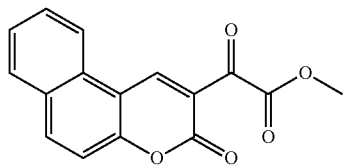 [SMILES: COC(=O)C(=O)c1cc2c(ccc3ccccc32)oc1=O]

5.00 g (22.00 mmoles) of 1,4-dimethyl (2E)-2-(piperidin-1-yl)but-2-enedioate and 3.79 g (22.01 mmoles) of 2-hydroxy-1-naphthadehyde were melted under stirring at 80° C. Then 5.5 mL of acetic acid were added to the mixture. The reaction temperature was raised up to 110° C. and the mixture stirred for 1.5 hours. After completion of the reaction, the mixture was cooled to 35-40° C., dissolved in 200 mL of dichloromethane and washed with 400 mL (x2) of water. The organic layer was dried over anhydrous sodium sulfate, filtered and the solvent removed by distillation under vacuum. The crude product was purified by flash column chromatography on silica gel (toluene/EtOAc 95:5) followed by crystallization from toluene obtaining 1.20 g of a yellow solid (yield 19%).

¹H-NMR (DMSO-d6, δ ppm): 3.91 (s, 3H), 7.67-7.73 (m, 2H), 7.83 (m, 1H), 8.12 (d, 1H), 8.43 (d, 1H), 8.72 (d, 1H), 9.57 (s, 1H).

Example 11

Synthesis of 2-ethylhexyl 2-oxo-2-(3-oxo-3H-benzo[f]chromen-2-yl)acetate

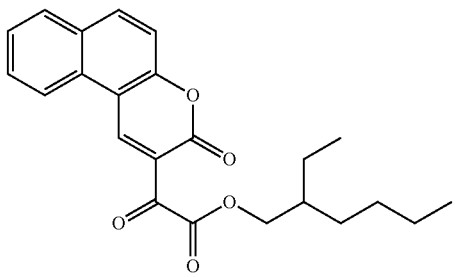 [SMILES: CCCCC(CC)COC(=O)C(=O)c1cc2c(ccc3ccccc32)oc1=O]

0.19 g (0.39 mmoles) of zirconium(IV) acetylacetonate were added under stirring to a warm solution of 1.10 g (3.90 mmoles) of methyl 2-oxo-2-(3-oxo-3H-benzo[f]chromen-2-yl)acetate and 1.27 g (9.75 mmoles) of 2-ethyl-1-hexanol in 25 mL of toluene. The reaction mixture was stirred at 105° C. for 2 hours eliminating methanol by distillation. Progress of the reaction was monitored by TLC. After completion of the reaction, the mixture was allowed to cool, diluted with dichloromethane and washed in sequence with 1M hydrochloric acid and brine. The organic layer was dried over anhydrous sodium sulfate, filtered and the solvent removed by distillation under vacuum. The crude product was purified by flash column chromatography on silica gel (toluene/ EtOAc 97.5:2.5) obtaining 1.33 g of a yellow solid (yield 90%).

$^1$H-NMR (DMSO-d$_6$, δ ppm): 0.76-0.91 (m, 6H), 1.18-1.42 (m, 8H), 1.68 (m, 1H), 4.25 (d, 2H), 7.65-7.73 (m, 2H), 7.83 (m, 1H), 8.12 (d, 1H), 8.42 (d, 1H), 8.70 (d, 1H), 9.54 (s, 1H).

Comparative Tests

The coumarin glyoxylates of the invention, were compared with ethyl 2-(9H-fluoren-2-yl)-2-oxo-acetate (COMP-1) and ethyl 2-oxo-2-thianthren-2-yl-acetate (COMP-2) of the prior art prepared as described in WO2018/041935.

Example 12.1

Comparative Tests

Example 12.1.1

Clear Formulation

The photopolymerizable compositions for the test were prepared dissolving the photoinitiators and the co-initiator, Esacure® EDB (IGM Resins B. V.) at a concentration of 3% by weight (wt) each in a mixture 99.5:0.5 wt of Ebecryl® 605 and Ebecryl® 350 (Allnex).

The photopolymerizable compositions placed in the sample lodgment of a FT-IR (FT-IR 430-Jasco), were exposed to a LED lamp (400 nm) located at a distance of 25 mm from the sample and at an angle of 30°. IR spectra were acquired at constant time intervals during the photopolymerization and the reduction over the time of the area of the peaks at 1408 and 810 cm$^{-1}$ assigned to the acrylic double bonds was determined using the IR software. This allows quantifying the degree of polymerization and therefore the efficiency of the photoinitiator.

The results expressed as % of polymerization over time, are reported in Table 1.

TABLE 1

| Photoinitiator | after 0.5" | after 2" |
|---|---|---|
| COMP-1* | 42 | 40 |
| COMP-2* | 14 | 27 |
| Example 1 | 54 | 58 |
| Example 7 | 55 | 63 |
| Example 11 | 27 | 37 |

* Comparative

These tests confirm that compounds of formulas (I) and (Ia) have a reactivity comparable or superior than the comparatives (COMP-1 and COMP-2), when use in the same amount.

Example 12.1.2

Cyan Inkjet Ink LED Lamp (400 nm)

The photopolymerizable compositions for the test were prepared dissolving the photoinitiators and the co-initiator, Esacure® EDB (IGM Resins B. V.) at a concentration of 5% by weight (wt) each in a Cyan Inkjet Ink.

The photopolymerizable compositions placed in the sample lodgment of a FT-IR (FT-IR 430-Jasco), were exposed to a LED lamp (400 nm) located at a distance of 25 mm from the sample and at an angle of 30°. IR spectra were acquired at constant time intervals during the photopolymerization and the reduction over the time of the area of the peaks at 1408 and 810 cm$^{-1}$ assigned to the acrylic double bonds was determined using the IR software. This allows quantifying the degree of polymerization and therefore the efficiency of the photoinitiator.

The results expressed as % of polymerization over time, are reported in Table 2.

TABLE 2

| Photoinitiator | after 0.5" | after 2" |
|---|---|---|
| COMP-1* | 15 | 19 |
| COMP-2* | 0 | 0 |
| Example 1 | 71 | 75 |
| Example 2 | 26 | 51 |
| Example 3 | 25 | 34 |
| Example 7 | 56 | 66 |
| Example 11 | 15 | 47 |

*Comparative

These tests confirm the high reactivity of compounds of formulas (I) and (Ia) also in pigmented systems.

Example 12.1.3

Tack-Free in Clear Formulation

The photopolymerizable compositions for the test were prepared dissolving the photoinitiators and the co-initiator, Esacure® A198 (IGM Resins B. V.) at a concentration of 4% by weight (wt) each in:

Formulation A—Photomer® 6577 50% by wt, Photomer® 4335 15% by wt, Photomer® 4666 15% by wt, Photomer® 4172 20% by wt;

Formulation B—Photomer® 3016 50% by wt, Photomer® 4335 15% by wt, Photomer® 4666 15% by wt, Photomer® 4172 20% by wt;

Formulation C—Photomer® 5442 50% by wt, Photomer® 4335 15% by wt, Photomer® 4666 15% by wt, Photomer® 4172 20% by wt;

Formulation D—Photomer® 6628 50% by wt, Photomer® 4335 15% by wt, Photomer® 4666 15% by wt, Photomer® 4172 20% by wt.

Formulation E for the test was prepared dissolving the photoinitiators at a concentration of 4% by weight (wt) in the following composition: Photomer® 5662 50% by wt, Photomer® 4335 15% by wt, Photomer® 4666 15% by wt, Photomer® 4172 20% by wt (i.e. Formulation E does not comprise a co-initiator).

The photopolymerizable compositions were applied with a thickness of 6 micron, by a K101 control coater on a paper support, then passed under an LED lamp at 395 nm (16 W/cm). The tack-free was measured and the results expressed in meters per minutes, are reported in Table 3. Greater the speed (m/min) better the performance.

TABLE 3

| Photoinitiator | Form. A m/min | Form. B m/min | Form. C m/min | Form. D m/min | Form. E m/min |
|---|---|---|---|---|---|
| COMP-1* | 24 | 15 | 30 | 33 | 36 |
| COMP-2* | 10 | — | — | — | — |
| Example 1 | 76 | 52 | 94 | 98 | 99 |
| Example 7 | 99 | 76 | >100 | >100 | >100 |

*Comparative

Formulation A was also exposed at an LED lamp at 365 nm (12 W/cm), the tack-free was measured, the results expressed in meters per minutes are reported in Table 4

TABLE 4

| Photoinitiator | LED lamp 395 nm m/min | LED lamp 365 nm m/min |
|---|---|---|
| COMP-1* | 24 | 37 |
| COMP-2* | 10 | 10 |
| Example 1 | 76 | 72 |
| Example 7 | 99 | 97 |

*Comparative

These tests confirm that compounds of formulas (I and Ia) are more reactive than the comparatives in many different formulations and at different LED wavelengths.

Example 12.1.4

Through Cure in Cyan Offset Ink

The photopolymerizable compositions for the test were prepared dissolving the photoinitiators and the coinitiator, Esacure® A198 (IGM Resins B. V.) at a concentration of 1.5% by weight (wt) each in a Cyan Offset Ink. The photopolymerizable compositions were applied with a thickness of 1.5 micron on a paper support, then passed under an LED lamp at 395 nm (16 W/cm) or at 365 nm (12 W/cm). The through cure was measured and the results, expressed in meters per minutes, are reported in Table 5. Greater the speed (m/min) better the performance.

TABLE 5

| Photoinitiator | LED lamp 395 nm m/min | LED lamp 365 nm m/min |
|---|---|---|
| COMP-1* | <10 | 25 |
| COMP-2* | <10 | <10 |
| Example 1 | 65 | 60 |
| Example 7 | 73 | 77 |

*Comparative

All the above tests confirm the outstanding performance of compounds of formulas (I) and (Ia), even in case of low thickness and pigmented systems.

The invention claimed is:

1. A photocurable composition comprising:
   (a) from 50 to 99.9% by weight, based on the total content of the composition, excluding possible water and solvents, of at least one ethylenically unsaturated compound;
   (b) from 0.1 to 35% by weight, based on the total content of the composition, excluding possible water and solvents, of at least one compound of formula (I)

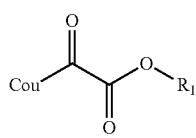

I wherein:
$R_1$ is a substituted or unsubstituted C1-C20 alkyl group or a substituted or unsubstituted C1-C50 alkyl group which is interrupted by one or more oxygens and may terminate with a hydroxy group or with an alkyl residue;

Cou is a coumarin group of formula:

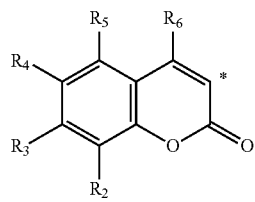

(A)

wherein:
$R_2$, $R_3$, $R_4$ and $R_5$ are, independently of one another, hydrogen, substituted or
unsubstituted C1-C20 alkyl, -N(C1-C6 alkyl)$_2$, piperidino, morpholino, piperazino, —O—$R_7$ or —S—
$R_7$, where $R_7$ is hydrogen, substituted or unsubstituted C1-C20 alkyl, C2-C12 alkenyl, substituted
or unsubstituted aryl, heteroaryl or C5-C6 cycloalkyl;
$R_6$ is hydrogen, a hydroxy group or a C1-C4 alkyl group;
or Cou is a substituted or unsubstituted naphtho-coumarin group of formula:

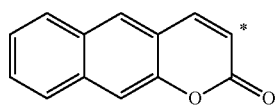

(B)

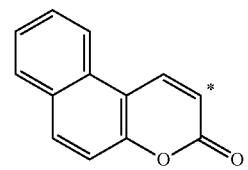

(C)

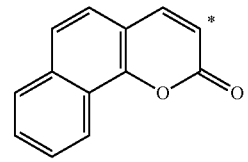

(D)

wherein the star indicates the carbon atom which is bound to the keto group of formula (I).

2. The photocurable composition of claim 1, wherein formula (I) $R_1$ is a substituted or unsubstituted C1-C20 alkyl group.

3. The photocurable composition of claim 1 wherein in formula (I) Cou is a coumarin group of formula (A) in which at least one of $R_2$, $R_3$, $R_4$ and $R_5$ is different from hydrogen.

4. The photocurable composition of claim 1, wherein formula (I) Cou is (A) and $R_6$ is hydrogen or Cou is (C).

5. The photocurable composition of claim 1, wherein in formula (I) Cou is a coumarin group of formula (A) in which $R_6$ is hydrogen,
at least two of $R_2$, $R_3$, $R_4$ and $R_5$ are —O—$R_7$ group and $R_7$ and $R_1$ are a C1-C20 alkyl group.

6. The photocurable composition of claim 1, further comprising:
   c) from 0.01 to 15% by weight of the total content of the composition, excluding possible water and solvents, of one or more photosensitizer; and/or
   d) from 0.2 to 15% by weight of the total content of the composition, excluding possible water and solvents, of accelerators/coinitiators; and/or e) from 0.5 to 15% by weight the total content of the composition, excluding possible water and solvents, one or more further photoinitiators; and/or f) conventional additives.

7. A process for photocuring photopolymerizable compositions and inks, which process comprises the following steps:

(i) providing a photopolymerizable composition comprising:

compounds (a) and (b); as defined in claim 1 or compounds (a), (b) as defined in claim 1, and one or more components selected from c) from 0.01 to 15% by weight of the total content of the composition, excluding possible water and solvents, of one or more photosensitizer; and/or d) from 0.2 to 15% by weight of the total content of the composition, excluding possible water and solvents, of accelerators/coinitiators; and/or e) from 0.5 to 15% by weight the total content of the composition, excluding possible water and solvents, one or more further photoinitiators; and/or f) conventional additives;

(ii) photopolymerizing the composition of step (i) with an light source.

8. The process of claim 7, wherein light source comprises UV light in at least one of the UVA, UVB and UVC ranges.

9. The process of claim 7, wherein light source is a LED source emitting in the range from 350 to 420 nm.

10. The process of claim 7, further comprising the step of applying said photopolymerizable composition to a substrate prior to photopolymerizing it.

11. The photocurable composition according to claim 1, comprising from 70 to 98.9% by weight, based on the total content of the composition, excluding water and solvents of at least one ethylenically unsaturated compound.

12. The photocurable composition according to claim 1, comprising from 0.1 to 20% by weight, based on the total content of the composition, excluding water and solvents of at least one compound of formula (I)

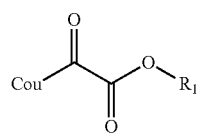

I

13. The photocurable composition according to claim 1, comprising from 0.2 to 15% by weight, based on the total content of the composition, excluding water and solvents of at least one compound of formula (I)

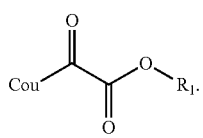

I

14. A compound of formula (Ia):

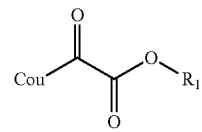

Ia wherein:

$R_1$ is a substituted or unsubstituted C1-C20 alkyl group or a substituted or unsubstituted C1-C50 alkyl group which is interrupted by one or more oxygens and may terminate with a hydroxy group or with an alkyl residue;

Cou is a coumarin group of formula:

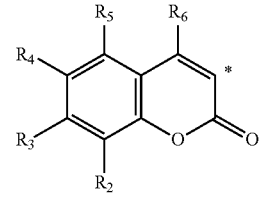

(A)

wherein:

$R_2$, $R_3$, $R_4$ and $R_5$ are, independently of one another, hydrogen, substituted or unsubstituted C1-C20 alkyl, -N(C1-C6 alkyl)$_2$, piperidino, morpholino, piperazino, —O—$R_7$ or —S—$R_7$, where $R_7$ is hydrogen, substituted or unsubstituted C1-C20 alkyl, C2-C12 alkenyl, substituted or unsubstituted aryl, heteroaryl or C5-C6 cycloalkyl;

$R_6$ is hydrogen, a hydroxy group or a C1-C4 alkyl group;

or Cou is a substituted or unsubstituted naphtho-coumarin group of formula:

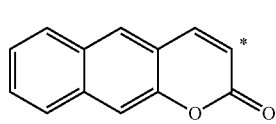

(B)

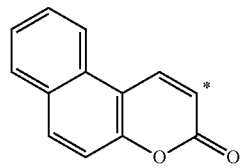

(C)

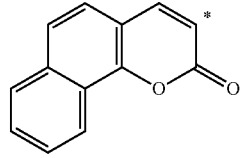

(D)

wherein the star indicates the carbon atom which is bound to the keto group of formula (Ia);

provided that:

when $R_1$ is methyl, than at least one of $R_2$, $R_3$, $R_4$, $R_5$ and $R_6$ is different from hydrogen;

when $R_1$ is methyl or ethyl, than $R_4$ is different from methyl;

when $R_1$ is methyl, than $R_6$ is not hydroxy;
when $R_1$ is methyl or ethyl, than $R_2$ is not methoxy; and
when $R_1$ is methyl or ethyl, than $R_2$ and $R_4$ are not both tert-butyl.

15. The compound of claim 14, wherein in formula (Ia) $R_1$ is a substituted or unsubstituted C1-C20 alkyl group.

16. The compound of claim 14, wherein in formula (Ia) Cou is a coumarin group of formula (A) in which $R_3$ is substituted or unsubstituted C1-C20 alkyl, —O—$R_7$ or —S—$R_7$, where C1-C20 alkyl.

17. The compound of claim 14, wherein in formula (Ia) Cou is (A) and $R_6$ is hydrogen or Cou is (C).

18. The compound of claim 14,
wherein in formula (Ia) Cou is a coumarin group of formula (A) in which $R_6$ is hydrogen, at least two of $R_2$, $R_3$, $R_4$ and $R_5$ are —O—$R_7$ group and $R_7$ and $R_1$ are a C1-C20 alkyl group.

* * * * *